United States Patent [19] [11] 4,183,924
Green et al. [45] Jan. 15, 1980

[54] 17α-CHLORO-17β-HYDROCARBONSULFI-NYL-1,4-ANDROSTADIENES AND THE CORRESPONDING 17β-HYDROCARBONSULFONYL DERIVATIVES AND THEIR USE AS ANTI-ACNE AGENTS

[75] Inventors: Michael J. Green, Kendall Park; Robert Tiberi, Englishtown, both of N.J.

[73] Assignee: Schering Corporation, Kenilworth, N.J.

[21] Appl. No.: 881,217

[22] Filed: Feb. 27, 1978

[51] Int. Cl.$^2$ .................... A61K 31/565; C07J 31/00
[52] U.S. Cl. ..................... 424/242; 260/239.55 R; 260/397.3; 260/397.45

[58] Field of Search ................. 260/239.55 R, 397.3, 260/397.45; 424/242; Steroids MS File/

[56] References Cited

U.S. PATENT DOCUMENTS 4,091,036  5/1978  Varma ..................... 260/397.3 X

*Primary Examiner*—Ethel G. Love
*Attorney, Agent, or Firm*—Elizabeth A. Bellamy; Mary S. King

[57] ABSTRACT

Novel 17α-chloro-17β-hydrocarbonsulfinyl and 17α-chloro-17β-hydrocarbonsulfonyl derivatives of 3-oxo-1,4-androstadienes and their use as anti-acne agents are described.

18 Claims, No Drawings

17α-CHLORO-17β-HYDROCARBONSULFINYL-1,4-ANDROSTADIENES AND THE CORRESPONDING 17β-HYDROCARBONSULFONYL DERIVATIVES AND THEIR USE AS ANTI-ACNE AGENTS

FIELD OF THE INVENTION

This invention relates to novel compositions-of-matter, to methods for their manufacture and methods for their use as anti-acne agents.

Specifically, this invention relates to novel 17α-chloro-17β-hydrocarbonsulfinyl and 17α-chloro-17β-hydrocarbonsulfonyl derivatives of 3-oxo-1,4-androstadienes useful as anti-acne agents. Further, this invention relates to pharmaceutical compositions comprising said derivatives, to methods for their manufacture, and to methods for their use in the treatment and control of acne vulgaris via topical, intralesional and oral routes.

Particularly, this invention relates to novel 17α-chloro-17β-hydrocarbonsulfonyl and 17α-chloro-17β-hydrocarbonsulfonyl derivatives of 3-oxo-1,4-androstadienes among which are included such compounds as 17α-chloro-17β-[R]-benzylsulfinyl-1,4-androstadiene-3,11-dione; 17α-chloro-17β-(p-chlorobenzylsulfinyl)-1,4-androstadiene-3,11-dione; 9α-fluoro-17α-chloro-17β-[R]-benzylsulfinyl-1,4-androstadiene-3,11-dione; 17α-chloro-17β-[R]-benzylsulfonyl-1,4-androstadiene-3,11-dione and the like.

This invention also relates to the process for the preparation of the 17α-chloro-17β-hydrocarbonsulfinyl derivatives of the 3-oxo-1,4-androstadienes.

GENERAL DESCRIPTION OF THE INVENTION COMPOSITION-OF-MATTER ASPECT

In its composition-of-matter aspect, this invention relates to novel 17α-chloro-17β-hydrocarbonsulfinyl and 17α-chloro-17β-hydrocarbonsulfonyl derivatives of 3-oxo-1,4-androstadienes. Particularly, this invention relates to novel steroids defined by the following Formula I:

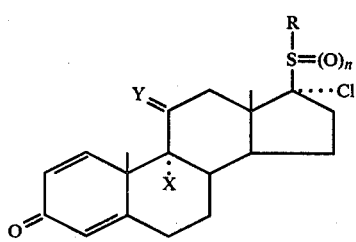

wherein R is benzyl, phenethyl, methylbenzyl, dimethylbenzyl, chlorobenzyl, dichlorobenzyl, and an alkyl group having up to 8 carbon atoms; X is hydrogen or fluorine; Y is oxygen, or hydrogen when X is hydrogen; and n is 1 or 2.

The compounds of our invention wherein R is methylbenzyl, dimethylbenzyl, chlorobenzyl or dichlorobenzyl are defined as those wherein the substituents methyl, dimethyl, chloro or dichloro can be in any position on the benzene ring. Furthermore, alkyl groups included in the definition of R may be straight or branched chain, e.g., methyl, ethyl, propyl, isopropyl, butyl, tert.-butyl and higher homologs such as pentyl, hexyl, heptyl and octyl.

Preferred compounds of our invention are those defined by the following formula II:

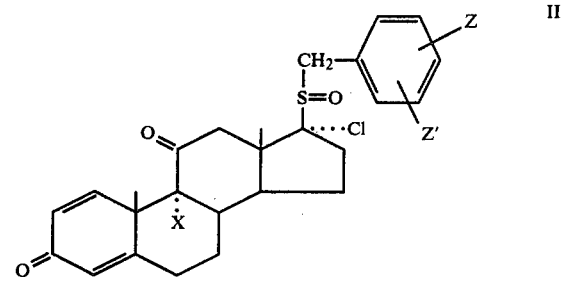

wherein X is as defined for Formula I, and Z and Z' are hydrogen, methyl or chlorine.

Exemplary compounds of this formula are:
(a) 17α-chloro-17β-[R]-benzylsulfinyl-1,4-androstadiene-3,11-dione,
(b) 17α-chloro-17β-(p-chlorobenzylsulfinyl)-1,4-androstadiene-3,11-dione,
(c) 17α-chloro-17β-(2',4'-dichlorobenzylsulfinyl)-1,4-androstadiene-3,11-dione,
(d) 17α-chloro-17β-(3',4'-dichlorobenzylsulfinyl)-1,4-androstadiene-3,11-dione,
(e) 17α-chloro-17β-(2'-methylbenzylsulfinyl)-1,4-androstadiene-3,11-dione,
(f) 9α-fluoro-17α-chloro-17β-[R]-benzylsulfinyl-1,4-androstadiene-3,11-dione.

Still other preferred compounds of this invention are those having the following Formula III:

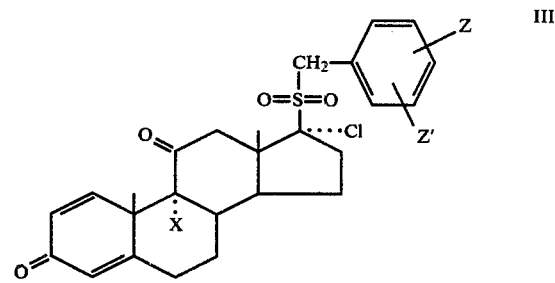

wherein X, Z and Z' are as defined in Formula II. Exemplary of such compounds is 17α-chloro-17β-benzylsulfonyl-1,4-androstadiene-3,11-dione.

Yet another embodiment of this invention are compounds having the following Formula IV:

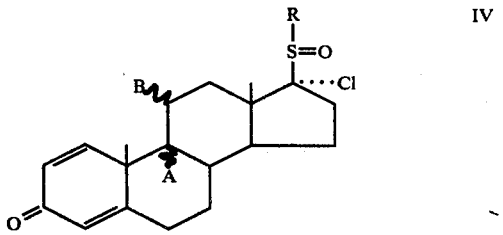

wherein R is as previously defined and wherein A is hydrogen, α-fluoro, α-bromo; B is hydroxyl, or together A and B form a 9β,11β-epoxy group or a 9(11) bond. Exemplary compounds of this formula are:
(a) 17α-chloro-17β-[R]-benzylsulfinyl-11β-hydroxy-1,4-androstadiene-3-one, (b) 17α-chloro-17β-[R]-benzylsulfinyl-11β-hydroxy-1,4,9(11)-androstatriene-3-one,
(c) 9α-bromo-17α-chloro-17β-[R]-benzylsulfinyl-11β-hydroxy-1,4-androstadiene-3-one,
(d) 9β,11β-epoxy-17α-chloro-17β-[R]-benzylsulfinyl-1,4-androstadiene-3-one,
(e) 9α-fluoro-17α-chloro-17β-[R]-benzylsulfinyl-11β-hydroxy-1,4-androstadiene-3-one.

It will be obvious to one skilled in the art that when n is 1 in Formula I, and in Formulae II and IV, there is an asymmetric center present at the sulfur atom. Therefore, our 17α-chloro-17β-hydrocarbonsulfinyl compounds may be in the R,S-form, in the R form, in the S form, or a mixture thereof. Where X-ray crystallographic techniques have confirmed the presence of specific stereochemistry, we have so indicated in the nomenclature of the compounds.

The physical embodiments of the compounds of this invention are characterized as being crystalline solids, usually white to off-white in color, which are insoluble in water and soluble in most organic solvents, particularly in acetone, dioxane, dimethylformamide, and dimethylsulfoxide, although of limited solubility in non-polar solvents such as dialkylethers and alkylhydrocarbons.

The 17α-chloro-17β-hydrocarbonsulfinyl and 17α-chloro-17β-hydrocarbonsulfonyl derivatives of the 3-oxo-1,4-androstadienes (Formulae I–III) inhibit sebaceous gland activity thereby making them useful as topical or oral anti-acne agents. Compounds of formula IV are useful as intermediates in the preparation of compounds of Formulae I–III.

PROCESS ASPECT OF THE INVENTION

The process aspect of this invention resides in the concept of preparing 3-oxo-1,4-androstadienes having substituents at C-17 of the following partial formula:

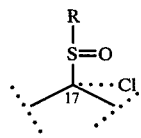

wherein R is benzyl, phenethyl, methylbenzyl, dimethylbenzyl, chlorobenzyl, dichlorobenzyl, and an alkyl group having up to 8 carbon atoms; which comprises reacting a 3-oxo-1,4-androstadiene having a substituent at C-17 of the following partial formula:

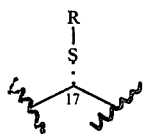

wherein R has the same meaning as above; with excess equivalents of a chlorine source in a mixture of water and a water soluble base, in a temperature range of from about −78° C. to about 25° C.

In brief, when carrying out our process, a 3-oxo-1,4-androstadiene having a 17α-thio function (e.g., 17α-benzylthio-1,4-androstadiene-3,11-dione) is dissolved in a mixture of water and a water soluble base (e.g., 20% aqueous pyridine), cooled to about −40° C. and treated with excess equivalents of a chlorine source (e.g., iodobenzene dichloride). The reaction is followed using thin layer chromatography (TLC) techniques to ascertain its conclusion, i.e., the absence of starting compound. Utilizing separation techniques known in the art, the 17α-chloro-17β-sulfinyl derivative of the 3-oxo-1,4-androstadiene is isolated (e.g., 17α-chloro-17β-[R]-benzylsulfinyl-1,4-androstadiene-3,11-dione).

Within the scope of our invention is included any chlorine or "positive" chlorine source; for example, chlorine gas, iodobenzene dichloride, N-chlorosuccinimide, 1-chlorobenzotriazole.

At least two equivalents of the chlorine source are necessary for optimization of the process, albeit 2 to about 5 equivalents of said chlorine source can be utilized. We have found that about 3 equivalents of the chlorine source maximize the yields of the desired compounds. Utilization of more than 5 equivalents of the chlorine source increases the possibility of producing excessively chlorinated compounds.

The solvent system is water and a water soluble base. If, however, solubility problems are encountered, organic diluents such as tetrahydrofuran, dioxane and the like may also be employed. Nitrogenous bases such as pyridine, trialkylamines, collidine and the like are preferred as the water soluble bases. However, inorganic water soluble bases such as sodium hydroxide, sodium methoxide, calcium hydroxide can also be used. Any amount of base used in the reaction will produce the 17α-chloro-17β-hydrocarbonsulfinyl compounds of our invention. However, to maximize the yields of product a minimum of 2 equivalents of base must be utilized. Obviously, since pyridine is preferentially used as the part of the solvent system, excessive quantities of base are not deleterious to the reaction.

The temperature range wherein the process can be conducted is about −78° C. to about ambient temperatures, preferably from about −40° C. to about 0° C. and usually at around −40° C. Prolonged reaction times at higher temperatures can produce excessive chlorination on the steroid molecule.

The reaction can be carried out over a period of 12–60 hours, but usually is completed in 18–36 hours. Absence of the starting material as determined by TLC indicates the conclusion of the reaction.

The 17α-thio derivatives of the 3-oxo-1,4-androstadienes utilized as the starting compounds in the process described hereinabove, although not specifically described in the prior art are derived by known chemical reactions. That is, nucleophilic substitution reactions by sulfides on leaving groups at $C_3$, $C_4$ and $C_6$ are known in the literature and analogous procedures may be applied to effect $C_{17}$ sulfide displacements. In one such procedure, sodium metal is dissolved in ethanol to which is added benzyl mercaptan and 17β-methanesulfonyloxy-1,4-androstadiene-3,11-dione, the mixture being refluxed for 72 hours. The resulting 17α-benzylthio-1,4-androstadiene-3,11-dione is isolated via standard techniques. In the foregoing reaction, solvents employed are preferably hydroxylic in nature such as methanol, ethanol, tert.-butanol and the like, or admixed with dipolar solvents (e.g., dimethylsulfoxide, dimethylformamide, hexamethylphosphoric triamide) or ethers (e.g., tetrahydrofuran, dioxane). The temperature employed may be from about 25° C. to reflux, but generally, reflux temperatures are employed. The reaction is continued until TLC of the reaction indicates absence of the starting material which usually takes 24 to 120 hours. Alkali metals used may be sodium or potassium. The mercaptan utilized will be dependent on the final product desired, and should be in at least 1 molar excess to the steroid but, generally, we use a 10 fold excess.

We have found it preferable to introduce the 17α-chloro-17β-hydrocarbonsulfinyl moieties into a 9-unsubstituted-3-oxo-1,4-androstadiene. After the foregoing moieties have been introduced, further chemical modifications may be necessary to obtain other compounds of our invention. As illustrated in Example 3 hereinbelow, other chemical reactions known in the steroid art may be used to introduce the 11β-hydroxy; the 9(11)-dehydro; the 9α-halogeno-11β-hydroxy moieties and the like. Further, as illustrated in Example 3, these chemical modifications will not destroy the stereochemical integrity of the sulfur atom unless, of course, a sulfinyl function is converted to a sulfonyl function.

The 17α-chloro-17β-hydrocarbonsulfonyl compounds of our invention are conveniently prepared from the corresponding 17α-chloro-17β-hydrocarbonsulfinyl derivatives by utilizing known oxidation techniques such as by using metachloroperbenzoic acid or hydrogen peroxide or peracetic acid and the like.

METHOD-OF-USE AND PHARMACEUTICAL COMPOSITION ASPECT

Our invention includes the method of treating and controlling acne which comprises applying either topically or intralesionally to the affected area, or by oral administration in a concentration effective for the treatment of acne, a steroid defined by formula I, together with a non-toxic, pharmaceutically acceptable carrier. Also included in our invention are pharmaceutical compositions comprising compounds of Formula I useful in the treatment and control of acne.

Acne is a common inflammatory disease in areas of the skin wherein sebaceous glands are largest, most numerous and most active. It is characterized by the appearance of comedones, pustles, papules, inflamed nodules and, in extreme cases, infected sacs.

It has been found in acne patients that sebum levels are elevated. Therefore, it has been postulated that sebum, which is a secretion of the sebaceous gland, is a causative agent in acne. Indeed, when sebum levels are reduced in acne patients, the condition is ameliorated. Some hormones used in anti-acne therapy can reduce sebaceous gland activity, but they, in turn, can and do demonstrate hormonal side effects.

Adolescents in puberty wherein there is a marked increase in hormonal production, are prime candidates for acne since androgen, a hormone produced at this time, has a major stimulatory effect on the sebaceous gland production of sebum.

Ideally, an anti-acne agent should be non-irritating and applicable topically or intralesionally, thereby eliminating the irritant effects such as encountered with Vitamin A acid treatment. An anti-acne agent can also be administered orally if it doesn't have the long-term systemic effects such as those manifested by tetracycline therapy, and the hormonal side effects produced by hormone therapy. By our invention, we have found such an anti-acne agent with anti-sebaceous gland activity.

As exemplified by Lutsky et al in the Journal of Investigative Dermatology, Vol. 64, pages 412–417 (1975) decrease of lipogenesis in the flank organ of the hamster is the animal model for the reduction of sebum production by the sebaceous gland. We have found that the compounds of our invention as illustrated by Formulae I-III, preferentially those of Formula II, best exemplified by 17α-chloro-17β-[R]-benzylsulfinyl-1,4-androstadiene-3,11-dione, have been found to reduce lipogenesis in the hamster flank organ, therefore, demonstrating anti-sebaceous gland activity. These compounds are therefore contemplated as novel and useful anti-acne agents. Advantageously, as stated before, the compounds of our invention are non-irritants and demonstrate no untoward systemic effects—hormonal or otherwise.

The method of treating or controlling acne utilizing the compounds of this invention is preferably carried out via topical routes, or, in case of severe acne, via intralesional routes. The compounds can also be administered orally. The actives are administered topically or orally in pharmaceutical compositions having the conventional carriers or excipients. The compositions may be in the form of lotions, creams, aerosols, ointments, solutions, gels, tablets and capsules. In these compositions, the active compound is preferably present in the range of from about 1% to about 20% by weight, administration being from about 2 to about 5 times daily.

Additionally, excessive sebum production is a causative factor in the condition-seborrheic dermatitis, otherwise known as "oily" skin. We, therefore, contemplate that the compounds of our invention in their topical or oral formulations may be useful in combating this condition.

The following Examples are illustrative of methods whereby the compounds of our invention can be prepared and the pharmaceutical compositions in which they may be admixed, it being understood that the invention is not to be limited thereby.

EXAMPLE 1

SULFIDE DISPLACEMENT AT CARBON-17

A. 17α-Benzylthio-1,4-Androstadiene-3,11-Dione

To 13.8 gm. of sodium metal dissolved in 1040 ml. of ethanol is added 47 ml. of benzyl mercaptan, followed by 21 gm. of 17β-methanesulfonyloxy-1,4-androstadiene-3,11-dione. Heat to reflux for 72 hours, then cool and filter off insoluble material. Concentrate the filtrate in vacuo to about 150 ml. and precipitate into 1500 ml. of water containing 150 ml. of a 5% aqueous solution of sodium hypochlorite. Extract three times with 500 ml. portions of chloroform which is then washed twice with water. Dry the chloroform extracts over $Na_2SO_4$, then vacuum concentrate to dryness. Dissolve the residue in a minimum amount of chloroform/ethyl acetate (1:1) and pass through 300 gm. of silica gel. Take 1 l. fractions utilizing ethyl acetate/chloroform/hexane (1:10:10). Combine desired fractions as determined by thin layer chromatography and evaporate to dryness. Crystallize the resultant residue from ethyl acetate/hexane to obtain the title compound; m.p. 134°–136° C.; $\lambda_{max}^{MeOH}$ 237 nm ($\epsilon = 17,100$); $[\alpha]_D^{26} + 152.5°$ (DMF).

B. 17α-(β-Phenylethylthio)-1,4-Androstadiene-3,11-Dione

To 2.25 gm. of sodium metal dissolved in 180 ml. of ethanol is added 8 ml. of β-phenylethyl mercaptan followed by 3 gm. of 17β-methanesulfonyloxy-1,4-androstadiene-3,11-dione. Heat the reaction at reflux for 48 hours. Obtain a residue in a manner similar to that described in Example 1A. Chromatograph the residue on a 300 gm. silica gel column eluting with chloroform/ethyl acetate (2:1). Combine the desired fractions as determined by thin layer chromatography, evaporate and crystallize the resultant residue from ether/hexane to obtain the title compound; m.p. 112°–115° C.

C. 17α-(1′-Pentylthio)-1,4-Androstadiene-3,11-Dione

To 3.75 gm. of sodium metal dissolved in 300 ml. of ethanol is added 15 ml. of n-pentylmercaptan followed by 5 gm. of 17β-methanesulfonyloxy-1,4-androstadiene-3,11-dione. Heat to reflux for 72 hours. Obtain a residue in a manner similar to that described in Example 1A. Chromatograph the residue on a 500 gm. silica gel column eluting with chloroform/ethyl acetate (9:1). In a manner similar to that described in Example 1A, isolate, reduce and crystallize the desired fractions from ether/hexane to obtain the title compound.

D. 17α-Methylthio-1,4-Androstadiene-3,11-Dione

To 6.9 gm. of sodium metal dissolved in 225 ml. of ethanol is added 30 ml. of methylmercaptan followed by 10 gm. of 17β-methanesulfonyloxy-1,4-androstadiene-3,11-dione. Heat at reflux for 18 hours. Cool the solution to 0° C., filter solids and crystallize from chloroform/hexane to obtain the title compound; m.p. 180°–183° C.; $[\alpha]_D^{26}+101.6°$ (DMF).

E. 17α-(4′-Chlorobenzylthio)-1,4-Androstadiene-3,11-Dione

To 1.38 gm. of sodium metal dissolved in 120 ml. of ethanol is added 6 ml. of 4-chlorobenzylmercaptan followed by 2.26 gm. of 17β-methanesulfonyloxy-1,4-androstadiene-3,11-dione. Heat at reflux for 96 hours. Obtain a residue in a manner similar to that described in Example 1A. Dissolve the residue in a minimum amount of chloroform and pass through a 200 gm. silica gel column. Elute with chloroform following the fractions by TLC. Combine the fractions, reduce, and crystallize the residue from ethyl acetate/hexane to obtain the title compound; m.p. 176°–180° C.

F. 17α-(2′,4′-Dichlorobenzylthio)-1,4-Androstadiene-3,11-Dione

To 1.04 gm. of sodium metal dissolved in 80 ml. of ethanol is added 5.55 ml. of 2,4-dichlorobenzylmercaptan followed by 1.5 gm. of 17β-methanesulfonyloxy-1,4-androstadiene-3,11-dione. Heat at reflux for 76 hours under an atmosphere of nitrogen. In a manner similar to that described in Example 1E, isolate the title compound.

G. 17α-(3′,4′-Dichlorobenzylthio)-1,4-Androstadiene-3,11-Dione

In a manner similar to that described in Example 1A, 3,4-dichlorobenzylmercaptan is reacted with 17β-methanesulfonyloxy-1,4-androstadiene-3,11-dione to obtain the title compound of this example; m.p.=131°–133° C.; $[\alpha]_D^{26}+150°$ (CHCl$_3$); $\lambda_{max}^{MeOH}$ 228 nm ($\epsilon$=26,000).

H. 17α-(2′-Methylbenzylthio)-1,4-Androstadiene-3,11-Dione

In a manner similar to that described in Example 1A, 2-methylbenzylmercaptan is reacted with 17β-methanesulfonyloxy-1,4-androstadiene-3,11-dione to obtain the title compound of this example.

I. 17α-Methylthio-11β-Hydroxy-1,4-Androstadiene-3-One

Dissolve 4.25 gm. of sodium metal in 90 ml. of isopropanol and 180 ml. of toluene. Saturate the solution with methyl mercaptan gas. Add 18 gm. of 17β-methanesulfonyloxy-11β-hydroxy-1,4-androstadiene-3-one dissolved in 270 ml. of dimethylsulfoxide. Heat the reactants for 18 hours at 110° C. Pour the reaction into water and extract the water with ethyl acetate. Wash the ethyl acetate extracts with water, then dry over Na$_2$SO$_4$. Filter the ethyl acetate extracts, reduce, and crystallize the residue from acetone to obtain the title compound; $[\alpha]_D^{26}+48.3°$ (DMF); $\lambda_{max}^{MeOH}$ 243 nm ($\epsilon$=15,000).

J. 17α-Benzylthio-1,4-Androstadiene-3-One

To 2.25 gm. of sodium metal dissolved in 185 ml. of ethanol is added 8.2 ml. of benzyl mercaptan followed by 3 gm. of 17β-methanesulfonyloxy-1,4-androstadiene-3-one. The reactants are heated to reflux for 48 hours. Pour the reaction mixture into 5% NaOH solution and extract with ethyl acetate. Wash the ethyl acetate extracts with water, dry over Na$_2$SO$_4$, and evaporate to a residue. The residue is purified on a 300 gm. silica gel column eluting with chloroform/ethyl acetate (2:1) to obtain the title compound.

EXAMPLE 2

CHLORINATION AT CARBON-17 AND SULFUR OXIDATION

A. 17α-Chloro-17β-[R]-Benzylsulfinyl-1,4-Androstadiene-3,11-Dione (1) Dissolve 8 gm. of 17α-benzylthio-1,4-androstadiene-3,11-dione in 240 ml. of 20% aqueous pyridine. Cool the solution to −40° C. and add 16.5 gm. of iodobenzene dichloride and maintain at −40° C. for 18 hours. Dilute with an equal volume of chloroform and wash two times with water. Dry the organic layer over Na$_2$SO$_4$, filter, and then vacuum concentrate to dryness. Crystallize the residue from acetone to obtain the title compound; $[\alpha]_D^{26}+111.6°$ (CHCl$_3$); $\lambda_{max}^{MeOH}$ 224 nm ($\epsilon$=21,200); C.D. $[\theta]_{337}^{MeOH}+2,800$, $[\theta]_{259}^{MeOH}-33,000$, $[\theta]_{225}^{MeOH}+149,000$.

(2) Dissolve 1 gm. of 17α-benzylthio-1,4-androstadiene-3,11-dione in 40 ml. of tetrahydrofuran and 7.35 ml. of 1 M aqueous Na$_2$CO$_3$ solution. Cool the solution to −40° C. and add 2.03 gm. of iodobenzene dichloride and maintain at −40° C. for 24 hours. Pour the reaction mixture into water, filter the precipitate, wash with water and air dry. Crystallize the precipitate from acetone to obtain the title compound.

(3) In a manner similar to the foregoing, obtain the title compound by substituting 10 ml. of water and 0.413 gm. of sodium methoxide for the 1 M aqueous Na$_2$CO$_3$.

B. 17α-Chloro-17β-(β-Phenylethylsulfinyl)-1,4-Androstadiene-3,11-Dione

Dissolve 0.42 gm. of 17α-(β-phenylethylthio)-1,4-androstadiene-3,11-dione in a mixture of 6.4 ml. of pyridine and 1.6 ml. of water. Chill the solution to −40° C. and add 0.822 gm. of iodobenzene dichloride, continue stirring at −40° C. for 18 hours. After 18 hours, treat the reaction in a manner similar to Example 2A, crystallizing from chloroform/hexane to obtain the title compound; m.p.=230° C.; nmr (dmso-d$_6$) δ 1.19 (C$_{13}$—CH$_3$, s), 1.45 (C$_{10}$—CH$_3$, s), 6.10 (C$_4$—H, d), 6.20 (C$_2$—H, dd), 7.66 (C$_1$—H, d), 7.27 (φ).

C.
17α-Chloro-17β-(1'-Pentylsulfinyl)-1,4-Androstadiene-3,11-Dione

In a manner similar to that described in Example 2A, react 0.81 gm. of 17α-(1'-pentylthio)-1,4-androstadiene-3,11-dione, 12.8 ml. of pyridine, 3.2 ml. of water and 1.7 gm. of iodobenzene dichloride. After concentration, pass the residue through a 100 gm. silica gel column eluting with chloroform/ethyl acetate (4:1). Crystallize from acetone/hexane to obtain the title compound; nmr (dmso-d$_6$) δ 1.10 (C$_{13}$—CH$_3$, s), 1.38 (C$_{10}$—CH$_3$, s), 6.05 (C$_4$—H, d), 6.15 (C$_2$—H, dd), 7.65 (C$_1$—H, d).

D.
17α-Chloro-17β-Methylsulfinyl-1,4-Androstadiene-3,11-Dione

In a manner similar to that described in Example 2A, react 2.4 gm. of 17α-methylthio-1,4-androstadiene-3,11-dione, 55.6 ml. of pyridine, 14.4 ml. of water and 5.76 gm. of iodobenzene dichloride. Pass the concentrated residue through a 250 gm. silica gel column, eluting first with chloroform and then with ethyl acetate. Evaporate the ethyl acetate eluates and crystallize from acetone/hexane to obtain the title compound; nmr (CDCl$_3$) δ 1.21 (C$_{13}$—CH$_3$, s), 1.45 (C$_{10}$—CH$_3$, s), 2.55 (S—CH$_3$, s), 6.10 (C$_4$—H, d), 6.20 (C$_2$—H, dd), 7.68 (C$_1$—H, d).

E.
17α-Chloro-17β-(4'-Chlorobenzylsulfinyl)-1,4-Androstadiene-3,11-Dione In a manner similar to that described in Example 2A, react 0.4 gm. of 17α-(4'-chlorobenzylthio)-1,4-androstadiene-3,11-dione, 8 ml. of pyridine, 2 ml. of water and 0.85 gm. of iodobenzene dichloride. Isolate as in Example 2D, utilizing a 50 gm. silica gel column, and crystallizing from chloroform/ethyl acetate/hexane to obtain the title compound; nmr (dmso-d$_6$) δ 0.83 (C$_{13}$—CH$_3$, s), 1.38 (C$_{10}$—CH$_3$, s), 4.02 (CH$_2$—φ, dd), 6.08 (C$_4$—H, d), 6.15 (C$_2$—H, dd), 7.65 (C$_1$—H, d), 7.43 (φ, q).

F.
17α-Chloro-17β-(2',4'-Dichlorobenzylsulfinyl)-1,4-Androstadiene-3,11-Dione In a manner similar to that described in Example 2A, react 0.476 gm. of 17α-(2',4'-dichlorobenzylthio)-1,4-androstadiene-3,11-dione, 16 ml. of pyridine, 4 ml. of water and 0.822 gm. of iodobenzene dichloride. After vacuum concentration, triturate the resultant residue with ether. Crystallize the resulting solids with methylene chloride/ether to obtain the title compound; nmr (dmso-d$_6$) δ 1.09 (C$_{13}$—CH$_3$, s), 1.39 (C$_{10}$—CH$_3$, s), 4.20 (CH$_2$φ, s), 6.04 (C$_4$—H, s), 6.09 (C$_2$—H, dd), 7.3 (H$_6$, s), 7.50 (H$_3$'H$_5$', s), 7.60 (C$_1$—H, d), M.S. [M+] 524, 526, 528.

G.
17α-Chloro-17β-(3',4'-Dichlorobenzylsulfinyl)-1,4-Androstadiene-3,11-Dione In a manner similar to that described in Example 2A, react 0.238 gms. of 17α-(3',4'-dichlorobenzylthio)-1,4-androstadiene-3,11-dione, 8 ml. of pyridine, 2 ml. of water and 0.411 gm. of iodobenzene dichloride. Purify the residue utilizing thin layer silica gel chromatography, developing with ethyl acetate/chloroform (1:4) and eluting with ethyl acetate. Crystallize the major band from ether to obtain the title compound; m.p.=249°–251° C.

H.
17α-Chloro-17β-(2'-Methylbenzylsulfinyl)-1,4-Androstadiene-3,11-Dione In a manner similar to that described in Example 2A, react 0.946 gm. of 17α-(2'-methylbenzylthio)-1,4-androstadiene-3,11-dione, 32 ml. of pyridine, 8 ml. of water and 1.6 gm. of iodobenzene dichloride. Slurry the residue with ethyl acetate/ether and filter to obtain the title compound; [α]$_D^{26}$+135° (CHCl$_3$); λ$_{max}^{MeOH}$ 228 nm (ε=22,000).

I.
17α-Chloro-17β-Methylsulfinyl-11β-Hydroxy-1,4-Androstadiene-3-One

In a manner similar to that described in Example 2A, react 0.475 gm. 17α-methylthio-11β-hydroxy-1,4-androstadiene-3-one, 12 ml. of pyridine, 3 ml. of water and 1.17 gm. of iodobenzene dichloride. Purify the residue by utilizing thin layer silica gel chromatography, developing with acetone/ethyl acetate/chloroform (6:47:47), and eluting with ethyl acetate. Crystallize from acetone/hexane to obtain the title compound; m.p. 230°–233° C. (decomp.); nmr (dmso-d$_6$) δ 1.40 (C$_{10}$ and C$_{13}$—CH$_3$, s), 2.47 (SCH$_3$, s), 4.28 (11α-H, mult.), 5.94 (C$_4$—H, d), 6.16 (C$_2$—H, dd), 7.29 (C$_1$—H, d).

J.
17α-Chloro-17β-Benzylsulfinyl-1,4-Androstadiene-3-One

In a manner similar to that described in Example 2A, react 0.47 gm. of 17α-benzylthio-1,4-androstadiene-3-one, 19.2 ml. of pyridine, 4.8 ml. of water and 0.988 gm. of iodobenzene dichloride. Maintain the reaction at −40° C. for 72 hours. Purify the residue by utilizing thin layer silica gel chromatography, developing with chloroform/ethyl acetate (2:1) and eluting with ethyl acetate to obtain the title compound; nmr (CDCl$_3$) δ 1.23 (C$_{10}$ and C$_{13}$—CH$_3$, s), 4.03 (CH$_2$φ, dd), 6.08 (C$_4$—H, d), 6.23 (C$_2$—H, dd), 7.05 (C$_1$—H, d), 7.35 (φ, s).

EXAMPLE 3

OTHER 17α-CHLORO-17β-SULFUR COMPOUNDS

A.
17α-Chloro-17β-[R]-Benzylsulfinyl-11β-Hydroxy-1,4-Androstadiene-3-One Stir 1.4 gm. of 17α-chloro-17β-[R]-benzylsulfinyl-1,4-androstadiene-3,11-dione in 100 ml. of methanol with 0.4 gm. of sodium borohydride for 15 minutes at 25° C. Acidify with 1 N aqueous HCl and pour into water. Filter the solids, wash with water and air dry. Crystallize the solids from chloroform/hexane to obtain the title compound; nmr (dmso-d$_6$) δ 1.40 (C$_{13}$—CH$_3$, s), 1.42 (C$_{10}$—CH$_3$, s), 4.02 (CH$_2$φ, dd), 4.30 (11α-H, mult.), 5.98 (C$_4$—H, d), 6.21 (C$_2$—H, dd), 7.35 (C$_1$—H, d), 7.40 (Ph, s).

B.
17α-Chloro-17β-[R]-Benzylsulfinyl-1,4,9(11)-Androstatriene-3-One

Dissolve 0.6 gm. of 17α-chloro-17β-[R]-benzylsulfinyl-11β-hydroxy-1,4-androstadiene-3-one in 6 ml. of dimethylformamide and 1.8 ml. of collidine. Stir the solution for 10 minutes at 25° C. with 0.6 ml. of 3.5% SO₂ in methanesulfonylchloride (w/v). Pour the solution into water, filter the solids, wash with water and air dry. Crystallize the solids from acetone to obtain the title compound; nmr (dmso-d₆) δ 1.11 ($C_{13}$—$CH_3$, s), 1.40 ($C_{10}$—$CH_3$, s), 4.07 ($CH_2Ph$, dd), 5.61 ($C_{11}$—H, mult.), 6.09 ($C_4$—H, d), 6.21 ($C_2$—H, dd), 7.45 ($C_1$—H, d).

C.
9α-Bromo-17α-Chloro-17β-[R]-Benzylsulfinyl-11β-Hydroxy-1,4-Androstadiene-3-One Dissolve 0.36 gm. of 17α-chloro-17β-[R]-benzylsulfinyl-1,4,9(11)-androstatriene-3-one in 12 ml. of tetrahydrofuran, 1.32 ml. of water and 0.078 ml. of 70% aqueous $HClO_4$. Add 0.156 gm. of N-bromosuccinimide and stir at 25° C. for 2 hours in the dark. Then add 1 ml. of 10% aqueous sodium metabisulfite solution and pour the total reaction mixture in water. Filter the solids and wash with water and air dry. Crystallize the solids from water/dimethylformamide to obtain the title product; nmr (dmso-d₆) δ 1.38 ($C_{13}$—$CH_3$, s) 1.65 ($C_{10}$—$CH_3$, s) 3.98 ($CH_2\phi$, s), 4.56 (11α-H, mult.), 5.91 ($C_4$—H, d), 6.05 ($C_2$—H, dd), 7.31 ($C_1$—H, d), 7.51 (Ph).

D.
9β,11β-Epoxy-17α-Chloro-17β-[R]-Benzylsulfinyl-1,4-Androstadiene-3-One Reflux 0.3 gm. of 9α-bromo-17α-chloro-17β-[R]-benzylsulfinyl-11β-hydroxy-1,4-androstadiene-3-one, 30 ml. of methanol, and 0.3 gm. of potassium acetate for 18 hours. Pour the solution into water, filter the solids, wash with water and air dry to obtain the title compound; nmr (CDCl₃) δ 1.38 ($C_{13}$—$CH_3$, s), 1.40 ($C_{10}$—$CH_3$, s), 3.21 (11α-H, mult.), 3.96 ($CH_2Ph$, dd), 6.13 ($C_4$-H), 6.15 ($C_2$—H, dd), 6.58 ($C_1$—H, d), 7.33 (Ph).

E.
9α-Fluoro-17α-Chloro-17β-[R]-Benzylsulfinyl-11β-Hydroxy-1,4-Androstadiene-3-One Dissolve 0.206 gm. of 9β,11β-epoxy-17α-chloro-17β-[R]-benzylsulfinyl-1,4-androstadiene-3-one in 3.5 ml. of 70% aqueous HF and stir at 0° C. for 3 hours. Then pour the solution into a saturated $Na_2CO_3$ solution and extract with chloroform. Wash the chloroform extracts with water, dry over $Na_2SO_4$ and then evaporate to a residue. Crystallize the residue from methanol to obtain the title compound; m.p. 270° C. (decomp.); nmr (dmso-d₆) δ 1.42 ($C_{13}$—$CH_3$, s), 1.54 ($C_{10}$—$CH_3$, s), 4.03 ($CH_2Ph$,dd), 4.20 (11α-H, mult.), 6.10 ($C_4$—H, d), 6.29 ($C_2$—H, dd), 7.33 ($C_1$—H, d), 7.44 (Ph).

F.
9α-Fluoro-17α-Chloro-17β-[R]-Benzylsulfinyl-1,4-Androstadiene-3,11-Dione Stir 50 mg. of 9α-fluoro-17α-chloro-17β-[R]-benzylsulfinyl-11β-hydroxy-1,4-androstadiene-3-one in 5 ml. of methylene chloride with 21 mg. of sodium acetate and 27.5 mg. of pyridinium chlorochromate for 2 hours at 25° C. Then filter through a small amount of silica gel, evaporate the filtrate to a residue. Crystallize the residue from chloroform/hexane to obtain the title compound; m.p. 260° C. (decomp.); nmr (CDCl₃) δ 1.20 ($C_{13}$—$CH_3$, s), 1.54 ($C_{10}$—$CH_3$, s), 4.08 ($CH_2Ph$, dd), 6.12 ($C_4$—H, d), 6.33 ($C_2$—H, dd), 7.40 (Ph), 7.43 ($C_1$—H, d).

G.
17α-Chloro-17β-Benzylsulfonyl-1,4-Androstadiene-3,11-Dione

Stir 45 mg. of 17α-chloro-17β-[R]-benzylsulfinyl-1,4-androstadiene-3,11-dione in 5 ml. of benzene with 45 mg. of metachloroperbenzoic acid at 25° C. for 1 hour. Dilute the reaction mixture with ethyl acetate and wash with 10% sodium metabisulfite solution, followed by water. Dry the organic layer over $Na_2SO_4$, then evaporate to a residue. Crystallize the residue from ethyl acetate/hexane to obtain the title compound; [M+] 472, 474; [M-PhCH₂SO₂+] 317, 319.

FORMULATIONS

| Formulation 1 - Cream-5% | |
|---|---|
| | mg/gm |
| 17α-Chloro-17β-[R]-benzylsulfinyl-1,4-androstadiene-3,11-dione | 50.0 |
| White Petrolatum, USP | 150.0 |
| Mineral Oil, USP | 60.0 |
| Cetylstearyl Alcohol | 72.0 |
| Cetomacrogol 1000 | 22.5 |
| 4-Chloro-m cresol | 1.0 |
| Purified Water USP to make | 1.0 g. |

| Formulation 2 - Ointment-5% | |
|---|---|
| | mg/gm |
| 17α-Chloro-17β-[R]-benzylsulfinyl-1,4-androstadiene-3,11-dione | 50.0 |
| Mineral oil, USP | 50.0 |
| Propylene Glycol, USP | 50.0 |
| Petrolatum USP to make | 1.0 g. |

| Formulation 3 - Solution-5% | |
|---|---|
| | mg/ml |
| 17α-Chloro-17β-[R]-benzylsulfinyl-1,4-androstadiene-3,11-dione | 50.0 |
| Alcohol, USP | 50.0 |
| Propylene Glycol, USP to make | 1.0 ml. |

| Formulation 4 - Lotion-5% | |
|---|---|
| | mg/ml |
| 17α-Chloro-17β-[R]-benzylsulfinyl-1,4-androstadiene-3,11-dione | 50.0 |
| Isopropyl Alcohol NF | 500.0 |
| Carbopol 934 | 3.0 |
| Sodium Hydroxide q.s. | |
| Purified Water to make | 1.0 ml. |

| Formulation 5 - Gel-5% | |
|---|---|
| | mg/g |
| 17α-Chloro-17β-[R]-benzylsulfinyl-1,4-androstadiene-3,11-dione | 50.0 |
| Alcohol, USP | 150.0 |
| Carbopol 940 | 30.0 |

-continued

| Formulation 5 - Gel-5% | |
|---|---|
| | mg/g |
| Propylene Glycol, USP | 150.0 |
| Diisopropanolamine sufficient | |
| Purified Water, USP to make | 1.0 g. |

| Formulation 6 - Intralesional-5% | |
|---|---|
| | mg/ml |
| 17α-Chloro-17β-[R]-benzylsulfinyl-1,4-androstadiene-3,11-dione (sterile precipitated) | 50.0 |
| Monobasic sodium phosphate | 6.0 |
| Dibasic Sodium Phosphate Anhydrous | 0.5 |
| Polysorbate 80, USP | 0.1 |
| Benzyl Alcohol, R | 9.0 |
| Sodium Chloride, USP | 2.5 |
| Methylparaben, USP | 1.3 |
| Propylparaben, USP | 0.2 |
| Sodium Carboxymethylcellulose, USP | 3.0 |
| Disodium Edetate, USP | 0.1 |
| Water for Injection, USP q.s. ad | 1.0 ml. |

| Formulation 7 - Tablet-50 mg. | |
|---|---|
| | mg/Tab |
| 17α-Chloro-17β-[R]-benzylsulfinyl-1,4-androstadiene-3,11-dione (micronized) | 50 |
| Lactose | 298 |
| Corn Starch | 25 |
| Corn Starch Base (10% in water) | 25 |
| Magnesium stearate | 2 |
| Total | 400 mg. |

| Formulation 8 - Capsule-50 mg. | |
|---|---|
| | mg/Tab |
| 17α-Chloro-17β-[R]-benzylsulfinyl-1,4-androstadiene-3,11-dione (micronized) | 50 |
| Lactose | 298 |
| Corn Starch | 50 |
| Magnesium stearate | 2 |
| Total | 400[x] mg. |

[x]Encapsulate in two-piece hard gelatin capsule

We claim:
1. A steroid having the formula:

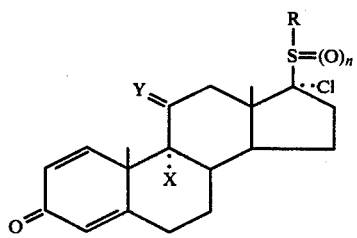

wherein R is benzyl, phenethyl, methylbenzyl, dimethylbenzyl, chlorobenzyl, dichlorobenzyl and an alkyl group having up to 8 carbon atoms; X is hydrogen or fluorine; Y is oxygen, or hydrogen when X is hydrogen, and n is 1 or 2.

2. A compound of claim 1 having the formula:

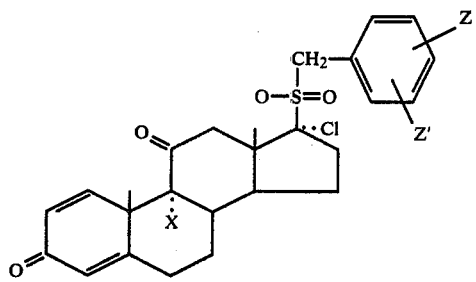

wherein X is fluorine or hydrogen, Z and Z' are hydrogen, methyl or chlorine.

3. A compound of claim 1 having the formula:

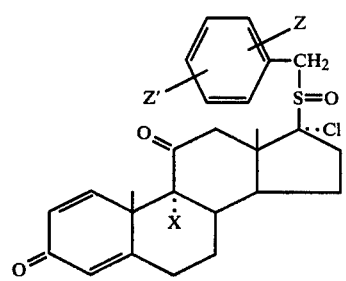

wherein X is fluorine or hydrogen, Z and Z' are hydrogen, methyl or chlorine.

4. A compound of claim 3 which is 17α-chloro-17β-[R]-benzylsulfinyl-1,4-androstadiene-3,11-dione.

5. A compound of claim 3 which is 17α-chloro-17β-(4'-chlorobenzylsulfinyl)-1,4-androstadiene-3,11-dione.

6. A compound of claim 3 which is 17α-chloro-17β-(2',4'-dichlorobenzylsulfinyl)-1,4-androstadiene-3,11-dione.

7. A compound of claim 3 which is 17α-chloro-17β-(3',4'-dichlorobenzylsulfinyl)-1,4-androstadiene-3,11-dione.

8. A compound of claim 3 which is 17α-chloro-17β-(2'-methylbenzylsulfinyl)-1,4-androstadiene-3,11-dione.

9. A compound of claim 3 which is 9α-fluoro-17α-chloro-17β-[R]-benzylsulfinyl-1,4-androstadiene-3,11-dione.

10. A steroid having the formula:

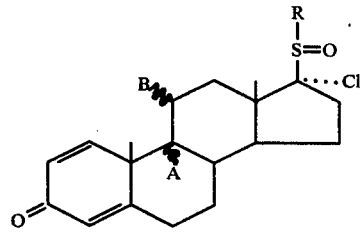

wherein A is hydrogen, α-fluoro, α-bromo; B is hydroxyl; or together A and B form a 9β,11β-epoxy group or a 9(11) bond; and R is benzyl, phenethyl, methylbenzyl, dimethylbenzyl, chlorobenzyl, dichlorobenzyl and an alkyl group having up to 8 carbon atoms.

11. The process for preparing a 3-oxo-1,4-androstadiene having a substituent at C-17 of the following partial formula:

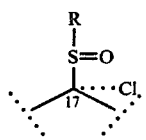

wherein R is benzyl, phenethyl, methylbenzyl, dimethylbenzyl, chlorobenzyl, dichlorobenzyl and an alkyl group having up to 8 carbon atoms; which comprises reacting a 3-oxo-1,4-androstadiene having a substituent at C-17 of the following partial formula:

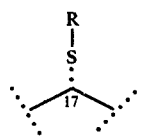

wherein R has the same meaning as above, with excess equivalents of a chlorine source in a mixture of water and a water soluble base, in the temperature range of from about −78° C. to about 25° C.

12. The process of claim 11 wherein said 3-oxo-1,4-androstadiene starting compound is a 9-unsubstituted-3,11-dioxo-1,4-androstadiene having a substituent at C-17 as defined in claim 11.

13. The process of claim 11 wherein said chlorine source is chlorine gas, iodobenzenedichloride, N-chlorosuccinimide or 1-chlorobenzotriazole.

14. The process of claim 11 wherein said water soluble base is a nitrogenous base selected from the group consisting of pyridine, trialkylamine or collidine.

15. The process of claim 11 wherein said temperature range is preferably about 0° C. to −40° C.

16. The process of claim 11 wherein said excess equivalents of chlorine source are in the range of from about 2–5 and wherein there are at least two equivalents of said water soluble base.

17. The method of treating and controlling acne which comprises applying either topically or intralesionally to the affected area, or by oral administration in a concentration effective for the treatment of acne, a steroid having the formula:

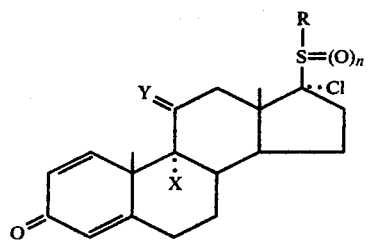

wherein R is benzyl, phenethyl, methylbenzyl, dimethylbenzyl, chlorobenzyl, dichlorobenzyl and an alkyl group having up to 8 carbon atoms; X is hydrogen or fluorine, Y is oxygen or hydrogen when X is hydrogen, and n is 1 or 2;

together with a non-toxic, pharmaceutically acceptable carrier.

18. A pharmaceutical composition for the treatment of acne comprising an anti-acne effective amount of a steroid having the formula:

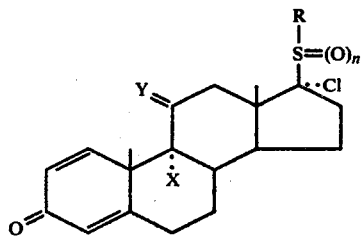

wherein R is benzyl, phenethyl, methylbenzyl, dimethylbenzyl, chlorobenzyl, dichlorobenzyl and an alkyl group having up to 8 carbon atoms; X is hydrogen or fluorine, Y is oxygen or hydrogen when X is hydrogen, and n is 1 or 2;

together with a non-toxic, pharmaceutically acceptable carrier.

* * * * *